United States Patent
Doyle et al.

(10) Patent No.: US 11,083,789 B2
(45) Date of Patent: Aug. 10, 2021

(54) IVIG TREATMENTS FOR BELL'S PALSY

(71) Applicant: InnoMed Technologies, Inc., Encino, CA (US)

(72) Inventors: Karen Doyle, Westlake Village, CA (US); John Joseph, Westlake Village, CA (US)

(73) Assignee: InnoMed Technologies, Inc., Encino, CA (US)

( * ) Notice: Subject to any disclaimer, the term of this patent is extended or adjusted under 35 U.S.C. 154(b) by 0 days.

(21) Appl. No.: 17/066,459

(22) Filed: Oct. 8, 2020

(65) Prior Publication Data

US 2021/0023210 A1    Jan. 28, 2021

Related U.S. Application Data

(63) Continuation of application No. PCT/US2020/017355, filed on Feb. 7, 2020.

(60) Provisional application No. 62/802,657, filed on Feb. 7, 2019.

(51) Int. Cl.
| | |
|---|---|
| *A61K 39/395* | (2006.01) |
| *A61P 21/00* | (2006.01) |
| *A61K 9/00* | (2006.01) |
| *A61K 31/573* | (2006.01) |

(52) U.S. Cl.
CPC .......... *A61K 39/395* (2013.01); *A61K 9/0019* (2013.01); *A61K 31/573* (2013.01); *A61P 21/00* (2018.01)

(58) Field of Classification Search
None
See application file for complete search history.

(56) References Cited

U.S. PATENT DOCUMENTS 10,144,776 B2 *  12/2018  Frey ................. A61P 25/18
2017/0044244 A1 *   2/2017  Frey ................. A61P 25/22

OTHER PUBLICATIONS

Wiles et al., Intravenous immunoglobulin in neurological disease; a specialist review, Apr. 1, 2002, J Neurobiololgy, Neurosurgery & Psychiatry 72(4):440-448 (Year: 2002).*
Murthy et al., Bell's palsy: Treatment guidelines, Jul. 2011, Annals of Indian Academy of Neurology 14(Suppl 1): S70-S72 (Year: 2011).*

* cited by examiner

*Primary Examiner* — John D Ulm
(74) *Attorney, Agent, or Firm* — Entralta P.C.; James F. Fleming; Peter D. Weinstein

(57) ABSTRACT

The present invention provides, among other aspects, methods and compositions for treating Bell's Palsy disease in a subject in need thereof, the method comprising: administering a therapeutically effective amount of a composition comprising human intravenous immunoglobulin (IVIG) to a subject. The present invention also provides, methods and composition for treating Bell's Palsy disease in a subject in need thereof, the method comprising: administering a therapeutically effective amount of a composition comprising human IVIG and a steroid. In certain aspects of the present invention the steroid is a cortical steroid, including Prednison.

15 Claims, No Drawings

IVIG TREATMENTS FOR BELL'S PALSY

CROSS REFERENCE TO RELATED APPLICATIONS

The present application is a national phase application of PCT/US20/17355 and claims priority to U.S. provisional patent application No. 62/802,657 filed on Feb. 7, 2019 the contents of which are incorporated by reference in its entirety.

BACKGROUND

The subject of this patent application relates generally to treatments for Bell's Palsy, and more particularly to Intravenous immunoglobulin (IVIG) treatments for Bell's Palsy.

By way of background, Bell's palsy involves an acute onset unilateral peripheral facial weakness, but the cause is unknown. The diagnosis can be established in patients with unexplained unilateral isolated facial weakness. The onset is of Bell's Palsy is rapid with symptoms generally at their worst within a few days. Furthermore, other symptoms may include pain in or behind the ear, numbness or tingling in the affected side of the face usually without any objective deficit on neurological examination, hyperacusis and disturbed taste on the ipsilateral anterior part of the tongue. Bilateral idiopathic facial palsy occurs less frequently than unilateral. Approximately, 7% of patients with a history of Bell's palsy may experience recurrence. The most common cause of acute onset unilateral peripheral facial weakness is Bell's palsy. The incidence of Bell's palsy is 20-30 cases for 100,000 and accounts for 60-70% of all cases of unilateral peripheral facial palsy and the median age is 40 years. Currently, the treatment protocol includes steroids, which may include antiviral therapy over a period of 2 weeks to 4 months.

Intravenous immunoglobulin (IVIG) is a blood product prepared from the serum of one or more donors. IVIG is used as an 'immunomodulatory' agent in an increasing number of immune and inflammatory disorders. Furthermore, IVIG is used to treat hematology related disorders, such as immune cytopenias, parvovirus B19 associated red cell aplasia, hypogammaglobulinaemia secondary to myeloma and chronic lymphatic leukaemia and post-bone marrow transplantation. In the field of immunology, IVIG is used in the treatment of primary antibody deficiency (PAD). In the field of nephrology, IVIG is used in the treatment of rheumatology. Additional new treatments employing IVIG are needed.

Applicant submits that more effective therapeutic treatments for Bell's Palsy patients are needed. In this aspect, IVIG has been disclosed herein as an improved treatment for Bell's Palsy and associated symptoms.

Applicant hereby incorporate herein by reference any and all patents and published patent applications cited or referred to in this application. Aspects of the present disclosure fulfill these needs and provide further related advantages as described in the following summary.

SUMMARY

Aspects of the present disclosure teach certain benefits in construction and use which give rise to the exemplary advantages described below.

In one aspect, the present disclosure solves the problems described above by providing a method for treating Bell's Palsy disease in a subject in need thereof, the method comprising: administering a therapeutically effective amount of a composition comprising human intravenous immunoglobulin (IVIG) to a subject.

Other features and advantages of aspects of the present disclosure will become apparent from the following more detailed description.

DETAILED DESCRIPTION

In one aspect, the present disclosure solves the problems described above by providing a method for treating Bell's Palsy disease in a subject in need thereof, the method comprising: administering a therapeutically effective amount of a composition comprising human intravenous immunoglobulin (IVIG) to a subject.

In another aspect, the present disclosure solves the problems described above by providing a method for treating Bell's Palsy disease in a subject in need thereof, the method comprising: administering a therapeutically effective amount of a composition comprising human intravenous immunoglobulin (IVIG) to a subject, and wherein the immunoglobulin is administered with a steroid.

Bell's palsy is generally characterized by a facial droop on one side of the face with a rapid onset within 48-72 hours. In rare cases (<1%), facial droop can occur on both sides resulting in total facial paralysis. Bell's Palsy results in an inability to control the facial muscles on the affected side resulting in facial paralysis. Symptoms can be mild to severe and may include muscle twitching, weakness, and/or total loss of the ability to move one or rarely both sides of the face. Additional symptoms include drooping of the eyelid, a change in taste, pain around the ear, and increased sensitivity to sound. The cause of Bell's Palsy is presently unknown. However, risk factors are known to include diabetes and/or a respiratory tract infection. Bell's Palsy results from a dysfunction of cranial nerve VII (facial nerve).

Diagnosis is based on a subject's physical appearance after ruling out other possible causes. Corticosteroids have been found to improve resolution of the disease and with some patients antiviral medications may provide an additional treatment benefit. Treatment can involve protecting the eye on the affected side from drying up with the use of eye drops or an eyepatch. Surgery is generally not recommended. Often, complete recovery is within six months with corticosteroids treatment. A small percentage of patients may not completely recover, or symptoms may recur. Bell's palsy typically occurs in subjects between ages 15 and 60 with no difference in gender. Familial genetics or inheritance has been found in about 4-14% of cases. Bell's Palsy is approximately four times more likely to occur in patients with diabetes. New cases of Bell's Palsy are about 20 per 100,000 population per year and the rate increases with age. Corticosteroids, such as prednisone generally improve recovery at 6 months and are regularly used for treatment. Early treatment (i.e., 3 days after onset) is needed for benefit of about a 14% greater probability of recovery.

The first step in the diagnosis of Bell's Palsy is to determine whether facial weakness is central or peripheral. Peripheral facial palsy involves all the facial muscles ipsilateral to the side of facial nerve involvement whereas central weakness involves lower facial muscles contralateral to the lesion in the brain stem above pons and cerebral hemisphere.

Diagnosis of Bell's palsy in a patient can include electrodiagnostic testing done within 14 days of onset and may provide prognostic information. The nerve excitability test determines the excitation threshold by recording the minimum electrical stimulus required to produce visible muscle contraction. A difference greater than 3.5 mA between affected and unaffected sides is considered to be significant in terms of poorer outcome. Measuring the peak-to-peak amplitude of the evoked compound action potential of the involved side compared to the normal side has prognostic importance. If there is a 90% or greater reduction in the amplitude of the affected side, the prognosis is poor.

Currently, the trigeminal blink reflex is the only test to measure intracranial pathway of the facial nerve, which is a test to study various post paralysis sequelae, such as synkinesis and hemifacial spasms.

The facial nerve is responsible for a number of functions, including blinking, closing the eyes, smiling, frowning, lacrimation, salivation, flaring nostrils, and raising eyebrows. The facial nerve transmits taste sensations from the anterior two-thirds of the tongue via the chorda tympani nerve. As a result, Bell's Palsy patients may present with a loss of taste sensation in the anterior ⅔ of the tongue on the affected side.

Patients with Bell's Palsy may present with a myriad of neurological symptoms, such as facial tingling, moderate or severe headache/neck pain, memory problems, balance problems, ipsilateral limb paresthesias, ipsilateral limb weakness, clumsiness, which do not suggest facia nerve involvement.

Approximately, 71% of Bell's Palsy patients have complete motor function recovery within about 6 months without treatment, and about one-third of patients suffer from residual effects from an incomplete recovery. However, some limiting factors include: old age, hypertension, diabetes mellitus, impairment of taste, and complete facial weakness. Residual effects can include post-paralytic hemifacial spasm, co-contracting muscles, synkinesis, sweating, lacrimation of the ipsilateral eye during chewing, and closure of the ipsilateral eyelid when the jaw opens. In case of incomplete or erroneous regeneration of the damaged facial nerve, but some bundles of smaller individual nerve connections may get sidetrack leading to a condition known as synkinesis. As a result, the regrowth of nerves controlling muscles attached to the eye may be sidetracked and regrow connections reaching the muscles of the mouth (i.e., when the person closes the eye, the corner of the mouth lifts involuntarily).

It is postulated that with Bell's Palsy that as a result of inflammation of the facial nerve, pressure is exerted on the nerve at the exit from the skull within the stylomastoid foramen, thereby blocking the transmission of neural signals and/or damaging the nerve.

Bell's palsy is a diagnosis of exclusion via the elimination of other diseases trauma, or conditions. Diagnoses typically includes assessing the degree of nerve damage with the House-Brackmann score.

The disclosure herein relates to treating Bell's Palsy patients with intravenous immunoglobulin (IVIG) with or without corticosteroids, whereby the patient's Bell's Palsy is resolved in less time than with corticosteroids alone or in combination with antivirals. In an embodiment, IVIG can be comprised of polyclonal antibodies, a monoclonal antibody, a mixture of different monoclonal antibodies, a mixture of polyclonal antibodies and a monoclonal antibody and/or polyclonal antibodies and a mixture of different monoclonal antibodies.

IVIG is recognized as a safe therapy without the side effects of steroids or other immunosuppressive agents. There have been numerous recent advances in our understanding of the mechanisms of action of IVIG and has been used in the fields of neurology, haematology, immunology, rheumatology, and dermatology.

Side effects of IVIG therapy are managed in some cases with premedication with analgesics and antihistamines and adjustment of the infusion rate. Therefore, as disclosed herein It will be important with IVIG to employ a minimum number of low doses to the patient, while providing rapid recovery from Bell's Palsy.

National bodies and medical associations have established varying standards for the use of immunoglobulin therapy.

Side effects of immunoglobulin infusions can include itching, rash, and hives. Moreover, more severe systemic side effects to immunoglobulin infusions can include an increased heart rate, hyper or hypotension, an increased body temperature, diarrhea, nausea, abdominal pain, vomiting, arthralgia or myalgia, dizziness, headache, fatigue, fever, and/or pain. Serious side effects of immunoglobulin infusions can include chest pain, myocardial infarction, tachycardia hyponatremia, hemolysis, hemolytic anemia, thrombosis, hepatitis, anaphylaxis, backache, aseptic meningitis, acute renal failure, hypokalemic nephropathy, pulmonary embolism, and transfusion related lung injury.

In order to avert less serious side effects, the patient's infusion rate can be adjusted lower to reduce or eliminate the side effects.

Commercial names of intravenous immunoglobulin formulations include Flebogamma®, Gamunex®, Privigen™, Octagam® and Gammagard®, HyQvia™, Hizentra™ (CSL Behring), Gamunex-C™, and Gammaked™.

Administration of the immunoglobulin formulations disclosed herein to a subject may be intravenous and/or subcutaneous. In some embodiments, the immunoglobulin is administered with a steroid. In some embodiments, the immunoglobulin is co-administered with a steroid, wherein the steroid is prednisone. In some embodiments, the immunoglobulin is co-administered with a steroid, wherein the steroid is prednisone administered in an amount between about 5 mg/day to 200 mg/day. In some embodiments, the IVIG is co-administered with a steroid, such as a cortical steroid and further, wherein an embodiment the steroid is prednisone, and wherein the prednisone is administered in an amount of, e.g. at least 10 mg/day, at least 20 mg/day, at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 210 mg/day, at least 220 mg/day, at least 230 mg/day, at least 240 mg/day, at least 250 mg/day, at least 260 mg/day, at least 270 mg/day, at least 280 mg/day, at least 290 mg/day, at least 300 mg/day, at least 310 mg/day, at least 320 mg/day, at least 330 mg/day, at least 340 mg/day, at least 350 mg/day, at least 360 mg/day, at least 370 mg/day, at least 380 mg/day, at least 390 mg/day, at least 400 mg/day, at least 410 mg/day, at least 420 mg/day, at least 430 mg/day, at least 440 mg/day, at least 450 mg/day, at least 460 mg/day, at least 470 mg/day, at least 480 mg/day, at least 490 mg/day, at least 500 mg/day, at least 510 mg/day, at least 520 mg/day, at least 530 mg/day, at least 540 mg/day, at least 550 mg/day, at least 600 mg/day, at least 650 mg/day, at least 700 mg/day, at least 750 mg/day, or at least 800 mg/day and wherein the IVIG is administered in an amount of at least 0.01 g/day, at least 0.05 g/day, at least 0.1 g/day, at least 0.5 g/day, at least 1 g/day, at least 2 g/day, at least 3 g/day, at least 4 g/day, at least 5 g/day, at least 6 g/day, at least 7 g/day, at least 8 g/day, at least 9 g/day, at least 10 g/day, at least 20 g/day, at least 30 g/day, at least 40 g/day, at least 50 g/day, at least 60 g/day, at least 70 g/day, at least 80 g/day, at least 90 g/day, at least 100 g/day, at least 110 g/day, at least 120 g/day, at least 130 g/day, at least 140 g/day, at least 150 g/day, at least 160 g/day, at least 170 g/day, at least 180 g/day, at least 190 g/day, at least 200 g/day, at least 210 g/day, at least 220 g/day, at least 230 g/day, at least 240 g/day, at least 250 g/day, at least 260 g/day, at least 270 g/day, at least 280 g/day, at least 290 g/day, at least 300 g/day, at least 310 g/day, at least 320 g/day, at least 330 g/day, at least 340 g/day, at least 350 g/day, at least 360 g/day, at least 370 g/day, at least 380 g/day, at least 390 g/day, at least 400 g/day, at least 410 g/day, at least 420 g/day, at least 430 g/day, at least 440 g/day, at least 450 g/day, at least 460 g/day, at least 470 g/day, at least 480 g/day, at least 490 g/day, at least 500 g/day, at least 510 g/day, at least 520 g/day, at least 530 g/day, at least 540 g/day, at least 5550 g/day, at least 600 g/day, at least 650 g/day, at least 700 g/day, at least 750 g/day, or at least 800 g/day.

In some embodiments, the IVIG is administered separately from a steroid, wherein the steroid is prednisone. In some embodiments, the IVIG is administered separately from a steroid, wherein the steroid is prednisone administered in an amount between, e.g. about 5 mg/day to 200 mg/day. In some embodiments, the IVIG is administered separately from a steroid, wherein the steroid is prednisone which in an embodiment is administered in an amount of at least 1 g/day, at least 10 g/day, at least 20 g/day, at least 30 g/day, at least 40 g/day, at least 50 g/day, at least 60 g/day, at least 70 g/day, at least 80 g/day, at least 90 g/day, at least 100 g/day, at least 110 g/day, at least 120 g/day, at least 130 g/day, at least 140 g/day, at least 150 g/day, at least 160 g/day, at least 170 g/day, at least 180 g/day, at least 190 g/day, at least 200 g/day, at least 210 g/day, at least 220 g/day, at least 230 g/day, at least 240 g/day, at least 250 g/day, at least 260 g/day, at least 270 g/day, at least 280 g/day, at least 290 g/day, at least 300 g/day, at least 310 g/day, at least 320 g/day, at least 330 g/day, at least 340 g/day, at least 350 g/day, at least 360 g/day, at least 370 g/day, at least 380 g/day, at least 390 g/day, at least 400 g/day, at least 410 g/day, at least 420 g/day, at least 430 g/day, at least 440 g/day, at least 450 g/day, at least 460 g/day, at least 470 g/day, at least 480 g/day, at least 490 g/day, at least 500 g/day, at least 510 g/day, at least 520 g/day, at least 530 g/day, at least 540 g/day, at least 5550 g/day, at least 600 g/day, at least 650 g/day, at least 700 g/day, at least 750 g/day, or at least 800 g/day; and wherein the prednisone is administered in an amount of at least 0.1 mg, at least 0.5 mg, at least 1 mg, at least 1.5 mg, at least 2 mg, at least 2.5 mg, at least 3 mg, at least 3.5 mg, at least 4 mg, at least 4.5 mg, at least 5 mg, at least 5.5 mg, at least 6 mg, at least 6.5 mg, at least 7 mg, at least 7.5 mg, at least 8 mg, at least 8.5 mg, at least 9 mg, at least 9.5 mg, at least 10 mg, at least 11 mg, at least 12 mg, at least 13 mg, at least 14 mg, at least 15 mg, at least 16 mg, at least 17 mg, at least 18 mg, at least 19 mg, at least 20 mg, at least 21 mg, at least 22 mg, at least 23 mg, at least 24 mg, at least 25 mg, at least 26 mg, at least 27 mg, at least 28 mg, at least 29 mg, at least 30 mg, at least 31 mg, at least 32 mg, at least 33 mg, at least 34 mg, at least 35 mg, at least 36 mg, at least 37 mg, at least 38 mg, at least 39 mg, at least 40 mg, at least 41 mg, at least 42 mg, at least 43 mg, at least 44 mg, at least 45 mg, at least 46 mg, at least 47 mg, at least 48 mg, at least 49 mg, at least 50 mg, at least 51 mg, at least 52 mg, at least 53 mg, at least 54 mg, at least 55 mg, at least 56 mg, at least 57 mg, at least 58 mg, at least 59 mg, at least 60 mg, at least 61 mg, at least 62 mg, at least 63 mg, at least 64 mg, at least 65 mg, at least 66 mg, at least 67 mg, at least 68 mg, at least 69 mg, at least 70 mg, at least 71 mg, at least 72 mg, at least 73 mg, at least 74 mg, at least mg, at least 76 mg, at least 77 mg, at least 78 mg, at least 79 mg, at least 80 mg, at least 81 mg, at least 82 mg, at least 83 mg, at least 84 mg, at least 85 mg, at least 86 mg, at least 87 mg, at least 88 mg, at least 89 mg, at least 90 mg, at least 91 mg, at least 92 mg, at least 93 mg, at least 94 mg, at least 95 mg, at least 96 mg, at least 97 mg, at least 98 mg, at least 99 mg, at least 100 mg, mg, at least 125 mg, at least 150 mg, at least 175 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, or at least 500 mg.

In some embodiments, the therapeutically effective amount of IVIG is between about at least 1 g/day, at least 10 g/day, at least 20 g/day, at least 30 g/day, at least 40 g/day, at least 50 g/day, at least 60 g/day, at least 70 g/day, at least 80 g/day, at least 90 g/day, at least 100 g/day, at least 110 g/day, at least 120 g/day, at least 130 g/day, at least 140 g/day, at least 150 g/day, at least 160 g/day, at least 170 g/day, at least 180 g/day, at least 190 g/day, at least 200 g/day, at least 210 g/day, at least 220 g/day, at least 230 g/day, at least 240 g/day, at least 250 g/day, at least 260 g/day, at least 270 g/day, at least 280 g/day, at least 290 g/day, at least 300 g/day, at least 310 g/day, at least 320 g/day, at least 330 g/day, at least 340 g/day, at least 350 g/day, at least 360 g/day, at least 370 g/day, at least 380 g/day, at least 390 g/day, at least 400 g/day, at least 410 g/day, at least 420 g/day, at least 430 g/day, at least 440 g/day, at least 450 g/day, at least 460 g/day, at least 470 g/day, at least 480 g/day, at least 490 g/day, at least 500 g/day, at least 510 g/day, at least 520 g/day, at least 530 g/day, at least 540 g/day, at least 5550 g/day, at least 600 g/day, at least 650 g/day, at least 700 g/day, at least 750 g/day, or at least 800 g/day.

In some embodiments, the therapeutically effective amount of IVIG is between about 0.1 g/kg to 10 g/kg of the subject, wherein the amount is administered in one or more doses during a two-week to eight-week period. In some embodiments, the therapeutically effective amount of IVIG is between about 0.1 g/kg to 10 g/kg of the subject administered over between about a two-week to eight-week period, wherein the amount is administered in one or more doses during the two-week to eight-week period. In some embodiments, the therapeutically effective amount of IVIG is between about 0.5 g/kg to 7 g/kg of the subject, wherein the amount is administered in one or more doses during a three-week to six-week period. In some embodiments, the therapeutically effective amount of IVIG is between about 0.5 g/kg to 7 g/kg of the subject, wherein the IVIG is administered in one dose. In some embodiments, the therapeutically effective amount of IVIG is between about 0.5 g/kg to 7 g/kg of the subject, wherein the immunoglobulin is administered in one dose, and wherein prednisone is administered in an amount between about 20 mg/day to 100 mg/day. In some embodiments, the therapeutically effective amount of IVIG is about 2 g/kg of the subject, wherein the immunoglobulin is administered in one dose, and wherein prednisone is administered in an amount of about 60 mg/day. In some embodiments, the composition is dispersed in a pharmaceutically acceptable solution.

Treatment during the acute phase of Bell's palsy includes strategies to reduce recovery time and to prevent corneal complications. Current strategies to speed recovery include physical therapy, corticosteroids and antiviral agents.

The rationale for the use of corticosteroids during the acute phase of Bell's palsy is that inflammation and edema of the facial nerve are implicated in causing Bell's palsy and corticosteroid's anti-inflammatory effects minimize nerve damage and thereby improve the outcome.

Randomized, double-blind, placebo-controlled trials have provided compelling evidence that treatment with prednisolone improves outcome in patients with Bell's palsy and shortens the time to complete recovery. Prednisolone should be used in all patients with facial palsy of less than 72 h duration who do not have contraindications to steroid therapy. The prednisolone dose used was 60 mg per day for 5 days then reduced by 10 mg per day and 50 mg per day for 10 days. In some embodiments, Bell's Palsy is 50-70% resolved within two weeks. In some embodiments, Bell's Palsy is completely resolved within two weeks. In some embodiments, Bell's Palsy symptoms are 50-70% reduced within two weeks. In some embodiments, Bell's Palsy symptoms are completely resolved within two weeks.

In other aspects of this embodiment, administration of IVIG with or without corticosteroids as disclosed herein reduces the severity of Bell's Palsy by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, administration of IVIG with or without corticosteroids as disclosed herein reduces the severity of Bell's Palsy from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A pharmaceutical composition disclosed herein comprising IVIG with or without a cortical steroid is administered in an amount sufficient to allow customary administration to an individual. In aspects of this embodiment, the IVIG disclosed herein may be administered at a dose of, e.g., at least 10 g, at least 20 g, at least 30 g, at least 40 g, at least 50 g, at least 60 g, at least 70 g, at least 80 g, at least 90 g, at least 100 m, at least 110 g, at least 120 g, at least 130 g, at least 140 g, at least 150 g, at least 160 g, at least 170 g, at least 180 g, at least 190 g, at least 200 .g, at least 210 g, at least 220 g, at least 230 g, at least 240 g, at least 250 g, at least 260 g, at least 270 g, or at least 280 g of IVIG. In other aspects of this embodiment, an IVIG with or without a cortical steroid as disclosed herein may be, e.g., at least 10 g, at least 20 g, at least 30 g, at least 40 g, at least 50 mg, at least 60 g, at least 70 g, at least 80 g, at least 90 g, at least 100 m, at least 110 g, at least 120 g, at least 130 g, at least 140 g, at least 150 g, at least 160 g, at least 170 g, at least 180 g, at least 190 g, at least 200 .g, at least 210 g, at least 220 g, at least 230 g, at least 240 g, at least 250 g, at least 260 g, at least 270 g, or at least 280 g of IVIG. In yet other aspects of this embodiment, IVIG with or without a cortical steroid as disclosed herein may be in the range of, e.g., about 10 g to about 280 g, about 50 g to about 250 g, about 75 g to about 225 g, about 100 g to about 200 g, about 75 g to about 200 g, about 50 g to about 225 g, about 100 g to about 250 g, about 80 g to about 225 g, about 80 g to about 200 g, about 90 g to about 250 g, about 90 g to about 225 g, or about 90 g to about 200 g.

IVIG with or without a cortical steroid as disclosed herein may comprise a solvent, emulsion or other diluent in an amount sufficient to dissolve IVIG with or without a cortical steroid as disclosed herein. In other aspects of this embodiment, IVIG with or without a cortical steroid as disclosed herein may comprise a solvent, emulsion or a diluent in an amount of, e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In other aspects of this embodiment, IVIG with or without a cortical steroid as disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of IVIG with or without a cortical steroid as disclosed herein may be of any concentration desired. In an aspect of this embodiment, the final concentration of IVIG with or without a cortical steroid in a pharmaceutical composition may be a therapeutically effective amount. In other aspects of this embodiment, the final concentration of IVIG with or without a cortical steroid in a pharmaceutical composition may be, e.g., at least 0.01 g/mL, at least 0.02 g/mL, at least 0.03 g/mL, at least 0.04 g/mL, at least 0.05 g/mL, at least 0.06 g/mL, at least 0.07 g/mL, at least 0.08 g/mL, at least 0.09 g/mL, at least 0.1 g/mL, at least 0.2 g/mL, at least 0.3 g/mL, at least 0.4 g/mL, at least 0.5 g/mL, at least 0.6 g/mL, at least 0.7 g/mL, at least 0.8 g/mL, at least 0.9 g/mL, at least 1 g/mL, at least 1.25 g/mL, g/mL, at least 1.5 g/mL, at least 1.75 g/mL, at least 2 g/mL, at least 2.25 g/mL, at least 2.5 g/mL, at least 2.75 g/mL, at least 3 g/mL, 3.25 g/mL, at least 3.5 g/mL, at least 3,75 g/mL, at least 4 g/mL, 4.25 g/mL, at least 4.5 g/mL, at least 4.75 g/mL, at least 5 g/mL, 5.25 g/mL, at least 5.5 g/mL, at least 5.75 g/mL, at least 6 g/mL, 6.25 g/mL, at least 6.5 g/mL, at least 6.75 g/mL, at least 7 g/mL, 7.25 g/mL, at least 7.5 g/mL, at least 7.75 g/mL, at least 8 g/mL, 8.25 g/mL, at least 8.5 g/mL, at least 8.75 g/mL, at least 9 g/mL, 9.25 g/mL, at least 9.5 g/mL, at least 9.75 g/mL, at least 10 g/mL. In other aspects of this embodiment, the concentration of IVIG with or without a cortical steroid as disclosed herein in the solution may be, e.g., at most 0.01 g/mL, at most 0.02 g/mL, at most 0.03 g/mL, at most 0.04 g/mL, at most 0.05 g/mL, at most 0.06 g/mL, at most 0.07 g/mL, at most 0.08 g/mL, at most 0.09 g/mL, at most 0.1 g/mL, at most 0.2 g/mL, at most 0.3 g/mL, at most 0.4 g/mL, at most 0.5 g/mL, at most 0.6 g/mL, at most 0.7 g/mL, at most 0.8 g/mL, at most 0.9 g/mL, at most 1 g/mL, at most 1.25 g/mL, g/mL, at most 1.5 g/mL, at most 1.75 g/mL, at most 2 g/mL, at most 2.25 g/mL, at most 2.5 g/mL, at most 2.75 g/mL, at most 3 g/mL, 3.25 g/mL, at most 3.5 g/mL, at most 3,75 g/mL, at most 4 g/mL, 4.25 g/mL, at most 4.5 g/mL, at most 4.75 g/mL, at most 5 g/mL, 5.25 g/mL, at most 5.5 g/mL, at most 5.75 g/mL, at most 6 g/mL, 6.25 g/mL, at most 6.5 g/mL, at most 6.75 g/mL, at most 7 g/mL, 7.25 g/mL, at most 7.5 g/mL, at most 7.75 g/mL, at most 8 g/mL, 8.25 g/mL, at most 8.5 g/mL, at most 8.75 g/mL, at most 9 g/mL, 9.25 g/mL, at most 9.5 g/mL, at most 9.75 g/mL, at most 10 g/mL. In other aspects of this embodiment, the final concentration of IVIG with or without a cortical steroid in a pharmaceutical composition may be in a range of, e.g., about 0.01 g/mL, about 0.02 g/mL, about 0.03 g/mL, about 0.04 g/mL, about 0.05 g/mL, about 0.06 g/mL, about 0.07 g/mL, about 0.08 g/mL, about 0.09 g/mL, about 0.1 g/mL, about 0.2 g/mL, about 0.3 g/mL, about 0.4 g/mL, about 0.5 g/mL, about 0.6 g/mL, about 0.7 g/mL, about 0.8 g/mL, about 0.9 g/mL, about 1 g/mL, about 1.25 g/mL, g/mL, about 1.5 g/mL, about 1.75 g/mL, about 2 g/mL, about 2.25 g/mL, about 2.5 g/mL, about 2.75 g/mL, about 3 g/mL, 3.25 g/mL, about 3.5 g/mL, about 3,75 g/mL, about 4 g/mL, 4.25 g/mL, about 4.5 g/mL, about 4.75 g/mL, about 5 g/mL, 5.25 g/mL, about 5.5 g/mL, about 5.75 g/mL, about 6 g/mL, 6.25 g/mL, about 6.5 g/mL, about 6.75 g/mL, about 7 g/mL, 7.25 g/mL, about 7.5 g/mL, about 7.75 g/mL, about 8 g/mL, 8.25 g/mL, about 8.5 g/mL, about 8.75 g/mL, about 9 g/mL, 9.25 g/mL, about 9.5 g/mL, about 9.75 g/mL, about 10 g/mL.

Aspects of the present specification disclose, in part, treating an individual suffering from Bell's Palsy. As used herein, the term "treating," refers to reducing or eliminating in an individual a clinical symptom of Bell's Palsy; or delaying or preventing in an individual the onset of a clinical symptom of Bell's Palsy. For example, the term "treating" can mean reducing a symptom of a condition characterized by Bell's Palsy, including, but not limited to, a reduction of, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. Those of skill in the art will know the appropriate symptoms or indicators associated with a Bell's Palsy and will know how to determine if an individual is a candidate for treatment as disclosed herein.

In aspects of this embodiment, a therapeutically effective amount of IVIG with or without a cortical steroid as disclosed herein reduces a symptom associated with Bell's Palsy by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of IVIG with or without a cortical steroid as disclosed herein reduces a symptom associated with Bell's Palsy by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of IVIG with or without a cortical steroid as disclosed herein reduces a symptom associated with Bell's Palsy by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of IVIG with or without a cortical steroid as disclosed herein generally is in the range of about 0.001 g/kg/day to about 10 g/kg/day. In aspects of this embodiment, an effective amount of IVIG with or without a cortical steroid as disclosed herein may be, e.g., at least 0.01 g/kg/day, at least 0.05 g/kg/day, at least 0.1 g/kg/day, at least 0.2 g/kg/day, at least 0.3 g/kg/day, at least 0.4 g/kg/day, at least 0.5 g/kg/day, at least 0.6 g/kg/day, at least 0.7 g/kg/day, at least 0.8 g/kg/day, at least 0.9 g/kg/day, at least 1 g/kg/day, at least 1.1 g/kg/day, at least 1.2 g/kg/day, at least 1.3 g/kg/day, at least 1.4 g/kg/day, at least 1.5 g/kg/day, at least 1.6 g/kg/day, at least 1.7 g/kg/day, at least 1.8 g/kg/day, at least 1.9 g/kg/day, at least 2 g/kg/day, at least 2.1 g/kg/day, at least 2.2 g/kg/day, at least 2.3 g/kg/day, at least 2.4 g/kg/day, at least 2.5 g/kg/day, at least 2.6 g/kg/day, at least 2.7 g/kg/day, at least 2.8 g/kg/day, at least 2.9 g/kg/day, at least 3 g/kg/day, at least 3.1 g/kg/day, at least 3.2 g/kg/day, at least 3.3 g/kg/day, at least 3.4 g/kg/day, at least 3.5 g/kg/day, at least 3.6 g/kg/day, at least 3.7 g/kg/day, at least 3.8 g/kg/day, at least 3.9 g/kg/day, at least 4 g/kg/day, at least 4.1 g/kg/day, at least 4.2 g/kg/day, at least 4.3 g/kg/day, at least 4.4 g/kg/day, at least 4.5 g/kg/day, at least 4.6 g/kg/day, at least 4.7 g/kg/day, at least 4.8 g/kg/day, at least 4.9 g/kg/day, at least 5 g/kg/day, at least 6 g/kg/day, at least 7 g/kg/day, at least 8 g/kg/day, at least 9 g/kg/day, or at least 10 g/kg/day. In other aspects of this embodiment, an effective amount of IVIG with or without a cortical steroid as disclosed herein may be in the range of, e.g., about 1 g/kg/day to about 10 g/kg/day, about 1 g/kg/day to about 7.5 g/kg/day, about 1 g/kg/day to about 6 g/kg/day, about 1 g/kg/day to about 5 g/kg/day, about 2 g/kg/day to about 10 g/kg/day, about 2 g/kg/day to about 7.5 g/kg/day, about 2 g/kg/day to about 6 g/kg/day, about 2 g/kg/day to about 5 g/kg/day, about 3 g/kg/day to about 10 g/kg/day, about 3 g/kg/day to about 7.5 g/kg/day, or about 3 g/kg/day to about 6 g/kg/day. In yet other aspects of this embodiment, an effective amount of IVIG with or without a cortical steroid as disclosed herein may be in the range of, e.g., about 1 g/kg/day to about 10 g/kg/day, about 1 g/kg/day to about 7.5 g/kg/day, about 1 g/kg/day to about 6 g/kg/day, about 1 g/kg/day to about 5 g/kg/day, about 2 g/kg/day to about 10 g/kg/day, about 2 g/kg/day to about 7.5 g/kg/day, about 2 g/kg/day to about 6 g/kg/day, about 2 g/kg/day to about 5 g/kg/day, about 3 g/kg/day to about 10 g/kg/day, about 3 g/kg/day to about 7.5 g/kg/day, or about 3 g/kg/day to about 6 g/kg/day. In still other aspects of this embodiment, an effective amount of IVIG with or without a cortical steroid as disclosed herein may be in the range of, about 1 g/kg/day to about 10 g/kg/day, about 1 g/kg/day to about 7.5 g/kg/day, about 1 g/kg/day to about 6 g/kg/day, about 1 g/kg/day to about 5 g/kg/day, about 2 g/kg/day to about 10 g/kg/day, about 2 g/kg/day to about 7.5 g/kg/day, about 2 g/kg/day to about 6 g/kg/day, about 2 g/kg/day to about 5 g/kg/day, about 3 g/kg/day to about 10 g/kg/day, about 3 g/kg/day to about 7.5 g/kg/day, or about 3 g/kg/day to about 6 g/kg/day.

In other aspects of this embodiment, an effective amount of IVIG with or without a cortical steroid as disclosed herein may be in the range of, e.g., about 1 g/kg/day to about 10 g/kg/day, about 1 g/kg/day to about 7.5 g/kg/day, about 1 g/kg/day to about 6 g/kg/day, about 1 g/kg/day to about 5 g/kg/day, about 2 g/kg/day to about 10 g/kg/day, about 2 g/kg/day to about 7.5 g/kg/day, about 2 g/kg/day to about 6 g/kg/day, about 2 g/kg/day to about 5 g/kg/day, about 3 g/kg/day to about 10 g/kg/day, about 3 g/kg/day to about 7.5 g/kg/day, or about 3 g/kg/day to about 6 g/kg/day. In yet other aspects of this embodiment, an effective amount of IVIG with or without a cortical steroid as disclosed herein may be in the range of, e.g., about 1 g/kg/day to about 10 g/kg/day, about 1 g/kg/day to about 7.5 g/kg/day, about 1 g/kg/day to about 6 g/kg/day, about 1 g/kg/day to about 5 g/kg/day, about 2 g/kg/day to about 10 g/kg/day, about 2 g/kg/day to about 7.5 g/kg/day, about 2 g/kg/day to about 6 g/kg/day, about 2 g/kg/day to about 5 g/kg/day, about 3 g/kg/day to about 10 g/kg/day, about 3 g/kg/day to about 7.5 g/kg/day, or about 3 g/kg/day to about 6 g/kg/day.

In liquid, semi-solid and solid formulations, a concentration of a Bell's Palsy therapeutic disclosed herein typically may be between about 0.001 g/mL to about 10 g/mL, about 0.001 g/mL to about 10 mg/mL, about 0.001 g/mL to about 5 mg/mL, about 0.5 g/mL to about 10 mg/mL, about 0.01 g/mL to about 10 g/mL, about 0.005 g/mL to about 10 mg/mL, about 0.005 g/mL to about 5 mg/mL, about 0.001 g/mL to about 6 g/mL, about 0.1 mg/mL to about 10 g/mL, about 0.1 g/mL to about 5 g/mL, about 0.5 g/mL to about 5 g/mL, about 1 g/mL to about 10 g/mL, about 2.5 g/mL to about 6 g/mL, about 3 g/mL to about 6 g/mL, about 4 g/mL to about 6 g/mL, about 1 g/mL to about 5 g/mL, about 1 g/mL to about 6 g/mL, about 2.5 g/mL to about 5 g/mL, about 3.5 g/mL to about 5 g/mL, about 4 g/mL to about 5 g/mL, about 3 g/mL to about 5 g/mL.

Dosing can be single dosage or cumulative (serial dosing), and can be readily determined by one skilled in the art. A Bell's Palsy therapeutic may be administered once, twice, three, four, five, six, seven, eight, nine, ten, eleven, twelve, thirteen, fourteen, fifteen, sixteen, seventeen, eighteen, nineteen, twenty or more times to a subject. For instance, treatment of Bell's Palsy may comprise a one-time administration of an effective dose of IVIG with or without a cortical steroid as disclosed herein. Alternatively, treatment of Bell's Palsy may comprise multiple administrations of an effective dose of IVIG with or without a cortical steroid as carried out over a range of time periods, such as, e.g., once daily, twice daily, trice daily, once every few days, or once weekly. The timing of administration can vary from individual to individual, depending upon such factors as the severity of an individual's symptoms. For example, an effective dose of IVIG with or without a cortical steroid as disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

In one embodiment, IVIG with or without a cortical steroid as disclosed herein is capable of decreasing the time to resolve the symptoms of Bell's Palsy in an individual suffering from a Bell's Palsy by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, IVIG with or without a cortical steroid as disclosed is capable of decreasing the time to resolve the symptoms of Bell's Palsy in an individual suffering from a Bell's Palsy by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In a further embodiment, IVIG with or without a cortical steroid and its derivatives have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, the period of administration of a Bell's Palsy therapeutic is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

In aspects of this embodiment, a therapeutically effective amount of IVIG with or without a cortical steroid as disclosed is capable of decreasing the time to resolve the symptoms of Bell's Palsy in an individual suffering from a Bell's Palsy by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100% as compared to a patient not receiving the same treatment.

IVIG with or without a cortical steroid or a Bell's Palsy therapeutic is administered to an individual. An individual is typically a human being, but can be an animal, including, but not limited to, dogs, cats, birds, cattle, horses, sheep, goats, reptiles and other animals, whether domesticated or not. Typically, any individual who is a candidate for treatment is a candidate with Bell's Palsy.

In an embodiment, in instances in which each of the Bell's Palsy therapeutics themselves are administered, without limitation, as individual or separate dosage forms (e.g., capsules, tablets or liquid), the kit comprises, without limitation, each of the Bell's Palsy therapeutics making up the composition of the invention, along with instructions for use. In an additional embodiment, the Bell's Palsy therapeutic components, without limitation, may be packaged in any manner suitable for administration, so long as the packaging, when considered along with the instructions for administration, without limitation, clearly indicates the manner in which each of the Bell's Palsy therapeutic components is to be administered. In a further embodiment, each of the Bell's Palsy therapeutics or a combination of such Bell's Palsy therapeutics may, without limitation, be combined into a single administrable dosage form such as a liquid, including a liquid administered subcutaneously or other liquid formulation. The Bell's Palsy therapeutic can be provided to an individual in a package. The package can be a container, for instance, without limitation, a bottle, a canister, a tube or other enclosed vessel. In an embodiment, the Bell's Palsy therapeutic is IVIG with or without a steroid, including, a cortical steroid, including prednisone.

EXAMPLES

The following non-limiting examples are provided for illustrative purposes only in order to facilitate a more complete understanding of representative embodiments now contemplated. These examples are intended to be a mere subset of all possible contexts in which the method for treating Bell's Palsy may be utilized. Thus, these examples should not be construed to limit any of the embodiments described in the present specification, including those pertaining to administering a therapeutically effective amount of a composition comprising human intravenous immunoglobulin (IVIG) to a subject and a steroid. Ultimately, the method for administering a therapeutically effective amount of a composition comprising human intravenous immunoglobulin (IVIG) to a subject and a steroid may be utilized in virtually any context where treating Bell's Palsy is desired.

Example 1

Treatment of 50-Year-Old Female Suffering from Bell's Palsy

The patient, a 50-year-old female was diagnosed by her doctor after claiming she is suffering from unexplained facial weakness. The patient's doctor diagnosed the patient as suffering from Bell's Palsy. The patient is put on 60 mg/day prednisone therapy and showed no reduction in the symptoms she suffers. Two weeks after administration, the patient is co-administered a single dose of IVIG at 2 g/kg and 60 mg prednisone and Bell's Palsy related symptoms the patient suffered from are reduced by 70% within two weeks from the co-administration.

Example 2

Treatment of a 48-Year-Old Male Suffering from Bell's Palsy

The patient, a 48-year-old male is diagnosed by his doctor as suffering from Bell's Palsy. The patient is put on 60 mg/day prednisone therapy for a period of a month and the Bell's Palsy did not resolve. The patient is then administered IVIG at 2 g/kg and 60 mg prednisone. Within three weeks, the Bell's Palsy is resolved by about 80%. The patient is then administered a second dose of IVIG at 2 g/kg and 60 mg. prednisone. Within two weeks, the patient is resolved by about 95%. A week later, the patient's Bell's Palsy symptoms have disappeared and the patient presents as normal.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A method for treating Bell's Palsy disease in a subject in need thereof, the method comprising: administering a therapeutically effective amount of a composition comprising human intravenous immunoglobulin (IVIG) to a subject, wherein the immunoglobulin is co-administered with a steroid.

2. The method of claim 1, wherein the steroid is prednisone.

3. The method of claim 1, wherein the steroid is prednisone administered in an amount between about 5 mg/day to 200 mg/day.

4. The method of claim 1, wherein the therapeutically effective amount of immunoglobulin is between about 0.1 g/kg to 10 g/kg of the subject.

5. The method of claim 1, wherein the therapeutically effective amount of immunoglobulin is between about 0.1 g/kg to 10 g/kg of the subject, wherein the amount is administered in one or more doses during a two-week to eight-week period.

6. The method of claim 1, wherein the therapeutically effective amount of immunoglobulin is between about 0.1 g/kg to 10 g/kg of the subject administered over between about a two-week to eight-week period, wherein the amount is administered in one or more doses during the two-week to eight-week period.

7. The method of claim 1, wherein the therapeutically effective amount of immunoglobulin is between about 2 g/kg to 7 g/kg of the subject, wherein the amount is administered in one or more doses during a three-week to six-week period.

8. The method of claim 1, wherein the therapeutically effective amount of immunoglobulin is between about 2 g/kg to 7 g/kg of the subject, wherein the immunoglobulin is administered in one dose.

9. The method of claim 1, wherein the therapeutically effective amount of immunoglobulin is between about 2 g/kg to 7 g/kg of the subject, wherein the immunoglobulin is administered in one dose, and wherein the steroid is prednisone and is administered in an amount between about 20 mg/day to 100 mg/day.

10. The method of claim 1, wherein the therapeutically effective amount of immunoglobulin is about 2 g/kg of the subject, wherein the immunoglobulin is administered in one dose, and wherein the steroid is prednisone and is administered in an amount of about 60 mg/day.

11. The method of claim 1, wherein the composition is dispersed in a pharmaceutically acceptable solution.

12. The method of claim 1, wherein Bell's Palsy is 50-70% resolved within two weeks.

13. The method of claim 1, wherein Bell's Palsy symptoms are 50-70% reduced within two weeks.

14. The method of claim 2, wherein the prednisone is provided to the subject at a dose of 60 mg.

15. The method of claim 2, wherein the IVIG is given to the subject at a dose of 2 g/kg body weight.

* * * * *